United States Patent [19]

Kerby et al.

[11] Patent Number: 5,364,980
[45] Date of Patent: Nov. 15, 1994

[54] PROCESS FOR THE PRODUCTION OF UNSYMMETRICAL TERT-DIALKYL ETHERS

[75] Inventors: Michael C. Kerby, Baton Rouge, La.; David E. W. Vaughan, Flemington, N.J.

[73] Assignee: Exxon Research & Engineering Co., Florham Park, N.J.

[21] Appl. No.: 816,318

[22] Filed: Dec. 30, 1991

[51] Int. Cl.$^5$ .............................. C07C 41/09
[52] U.S. Cl. .................................. 568/698
[58] Field of Search ......................... 568/698

[56] References Cited

U.S. PATENT DOCUMENTS 4,605,806  8/1986  Ballantine et al. .......... 568/698
5,099,072  3/1992  Knifton ...................... 568/698

FOREIGN PATENT DOCUMENTS 60-237035  11/1985  Japan ....................... 568/698

Primary Examiner—Howard T. Mars
Attorney, Agent, or Firm—Henry & Naylor

[57] ABSTRACT

A method for preparing unsymmetrical dialkyl ethers and derivatives thereof. The ethers are prepared by reacting a $C_1$ to $C_3$ aliphatic alcohol with a tertiary alcohol in the presence of a novel catalyst comprised of a transition metal pillared interlayered clay having generally separated layers wherein the interlayer distances are substantially greater than a precursor of the same but non-separated clay and wherein the product includes multimetallic pillars comprised of a cationic polymeric complex of the formula:

$$Al^{iv}(Al_{12-x}M_x)^{vi}O_4(OH)_{24}{}^{a+}$$

where x is a number from 1 to 6; a depends on the selection of M and N; N is selected from $Al^{3+}$, $Si^{4+}$, $Ga^{3+}$, $Ge^{4+}$, $As^{5+}$, $P^{5+}$, $Cr^{3+}$, $Fe^{3+}$, $V^{5+}$, $Ru^{3+}$, $Ru^{4+}$, $N^{3+}$; and M is selected from a metal from Groups 5B, 6B, 7B and 8 of the 4th, 5th and 6th Periods of the Periodic Table of the Elements.

11 Claims, No Drawings

PROCESS FOR THE PRODUCTION OF UNSYMMETRICAL TERT-DIALKYL ETHERS

FIELD OF THE INVENTION

The present invention relates to the preparation of unsymmetrical dialkyl ethers and derivatives thereof. The ethers are prepared by use of a novel catalyst comprised of a transition metal pillared interlayered clay.

BACKGROUND OF THE INVENTION

Motor gasoline formulations are expected to change in order to meet ever restrictive governmental regulations and competition from alternative fuels, such as methanol. One requirement of these reformulated gasolines is that they be substantially reduced in aromatics compounds, such as benzene. Furthermore, it is expected that governmental regulations will also substantially restrict the amount of light hydrocarbons which can be present, thus establishing the requirement that the gasoline be low in emissions.

While the removal of aromatics from gasolines is beneficial from an environmental point of view, their removal represents a substantial debit on motor octane number. This leaves the refiner in a position of finding a suitable substitute for aromatics from an octane number point of view, but which also meets the low emissions requirement.

One class of compounds which have been proposed for reformulated gasolines are oxygenates, such as the unsymmetrical dialkyl ethers, particularly methyl tert-butyl ether (MTBE), ethyl tert-butyl ether (ETBE), and tert-amyl methyl ether (TAME). If such compounds are to be extensively used in reformulated gasolines, then new and improved methods of their manufacture will be needed.

Conventional methods of manufacture of such ethers are typically based on liquid-phase reactions, such as the reaction of iso-butylene with methanol over cation-exchanged resins (e.g. Amberlyst 15. See *Hydrocarbon Processing*, Oct. 1984, p. 63). Metal exchanged conventional clays have been used to make ethers, such as the reaction of 1-alkenes to bis-sec-alkyl ethers (Adams, et al., *J. Catalysis*, 58, p. 252 (1979)); the reaction of ethanol with hex-1-ene (Ballantine et al., *J. Mol. Catalysis*, 26, p. 37 (1984)). However, in a comparison of ether formation from pentanol over exchanged and pillared clays, the pillared clays were much less active than the non-pillared clay catalysts (Diddams, et al., *J. Chem. Soc. Chem. Commun.*, p. 1340 (1984)). The projected shortage of isobutylene, and other $C_4$ and $C_5$ unsaturates as raw materials, provides an incentive for finding alternative reactions for producing such ethers.

One such alternative method is taught in U.S. Pat. No. 4,503,263 wherein an olefin and water in the gas phase, are reacted over a solid heterogeneous $C_{10}$ to $C_{18}$ perfluorinated alkanesulfonic acid superacid in the olefin and the water in the gas phase, but below about 120° C.

Other alternative approaches can be found in U.S. Pat. Nos. 4,822,921 and 4,827,048 wherein tertiary butyl alcohol is reacted with methanol. In accordance with the '921 patent, these alcohols are reacted in the presence of a catalyst comprised of an inert support, such as titania, having a phosphoric acid impregnated thereon. The catalyst of the '048 patent is a heteropolyacid, such as 12-tungstophosphoric acid or 12-molybdophosphoric acid, on an inert support, such as titania.

Also, copending application, having an Attorney Docket No. of OP-3637, entitled "PROCESS FOR THE PRODUCTION OF UNSYMMETRICAL TERT-DIALKYL ETHERS", discloses a process for preparing the unsymmetrical tert-dialkyl ethers by use of a catalyst comprised of boron trifluoride hydrates on porous inorganic supports.

While such alternative processes for producing ethers, such as MTBE, show promise and may have some commercial value, there is still a need in the art for other alternative processes for producing this potentially important class of ethers.

SUMMARY OF THE INVENTION

In accordance with the present invention, there is provided a process for preparing unsymmetrical dialkyl ethers, wherein one of the alkyl groups is a tertiary group, which process comprises reacting a $C_1$ to $C_3$ aliphatic alcohol with a tertiary alcohol, in the presence of a catalyst comprised of a transition metal pillared interlayered clay having generally separated layers wherein the interlayer distances are substantially greater than a precursor of the same but non-separated clay. An example is one wherein the product includes multimetallic pillars comprised of a cationic polymeric complex of the formula:

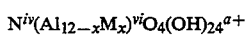

$$N^{iv}(Al_{12-x}M_x)^{vi}O_4(OH)_{24}{}^{a+}$$

where N is selected from $Al^{3+}$, $Si^{4+}$, $Ga^{3+}$, $Ge^{4+}$, $As^{5+}$, $P^{5+}$, $Cr^{3+}$, $Fe^{3+}$, $V^{5+}$, $Ru^{3+}$, $Ru^{4+}$, $Ni^{3+}$; and M is selected from Groups 5B, 6B, 7B and 8 of the 4th, 5th and 6th Periods of the Periodic Table of the Elements. These metals include V, Cr, Mn, Fe, Co, Ni, Nb, Mo, Te, Ru, Rh, Pd, Ta, W, Re, Os, Ir, an Pt. The value for "x" may be from 1 to 6 and "a" will depend on the nature of the metal substitutions.

In preferred embodiments of the present invention, N is Al, or Al and Ru, and M is selected from V, Cr, Mn, Fe, Co, Ni or a mixture thereof.

Another form of metal pillared clay is one that is exchanged with a metal cation solution after the $Al_{13}$ pillar is set.

Small spacing metal pillared materials have been described in U.S. Pat. No. 4,465,892 and by Brindley and Yamanaka (*Clays and Clay Minerals*, vol. 26, p.21 (1978); *Amer. Mineralogist*, vol. 64, p. 830 (1979)). Larger spacing metal oxide pillared materials have been described in U.S. Pat. No. 4,665,044. The many other possibilities in this system have been described in a review by Vaughan (*Amer. Chem. Soc. Symp. Proc.*, vol. 368, p. 308 (1988)).

It is further recognized that reaction of the forementioned metal modified $(Al_{13-x}M_x)$ clustered at temperatures between 60° and 120° C. may react to form smaller or larger polymers. Some of these may be more representative of hydrocalcite, or gibbsite type fragments having compositions in the range of $M_{(3-x)}Al_x(OH)_6{}^+$ or $Al_2M(OH_6)^{2+}$, where M is a divalent metal. Clusters of this type, or other clusters of a similar composition and cluster sizes, may have pillar spacings in the range of about 5 to 7 Å, giving pillared clay basal spacings in the range (001)=14Å to 16 Å. Alternatively, such reactions may generate larger polymer clusters and produce pillar spacings greater than about 8 Å to yield pillared clays having basal spacings with (001) greater than about 18 and up to about 30 Å.

The reaction can be represented by:

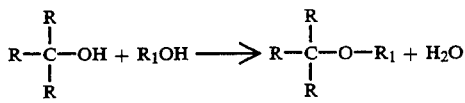

where each R is independently a $C_1$ to $C_5$ alkyl group; and $R_1$ is methyl, ethyl, propyl or butyl.

In another preferred embodiment of the present invention, two of the R groups are methyl and the third is selected from methyl, ethyl, and propyl.

In yet another preferred embodiment of the present invention, two of the R groups are methyl and the third is methyl or ethyl.

DETAILED DESCRIPTION OF THE INVENTION

The high octane/low emissions unsymmetrical dialkyl ethers of the present invention are those wherein one of the alkyl groups is a tertiary group. They are synthesized from alcohols, instead of iso-butylene aliphatic alcohol mixtures. The synthesis of these ethers is accomplished using a unique catalyst system with two classes of alcohols. One class of alcohol is an aliphatic alcohol represented by $R_1OH$, where $R_1$ is a $C_1$ to $C_3$ aliphatic alkyl group, preferably a methyl or ethyl group, more preferably a methyl group. The other class of alcohols are tertiary alcohols represented by:

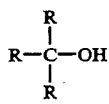

where each R is independently a $C_1$ to $C_5$ alkyl group, with the proviso that the total number of carbons not exceed about 7. Preferred is when two of the R groups is methyl and the other is selected from the group consisting of methyl, ethyl, propyl, or butyl. More preferred is when the other R group is a methyl or ethyl group.

The catalysts used in the synthesis of the ethers of the present invention are prepared from naturally occurring and synthetic smectites which may be visualized as a sandwich comprising two outer layers of silicon tetrahedra and an inner layer of aluminum octahedral. These clays are generally represented by the general formula:

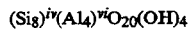

where the iv designation indicates an ion coordinated to four other ions, and the vi designates an ion coordinated to six other ions. The iv coordinated ion is commonly $Si^{4+}$, $Al^{3+}$, or $Fe^{3+}$, but could also include several other four-coordinate ions, e.g., $P^{5+}$, $B^{3+}$, $Ga^{3+}$, $Cr^{3+}$, $Ge^{4+}$, $Be^{2+}$, et. The vi coordinated ion is typically $Al^{3+}$ or $Mg^{2+}$, but could also include many other possible hexacoordinate ions, e.g., $Fe^{3+}$, $Fe^{2+}$, $Ni^{2+}$, $Co^{2+}$, $Li^+$, $Cr^{3+}$, $V^{2+}$, etc. The charge deficiencies created by substitutions into these cation positions are balanced by one or more cations located between the structure's platelets. Water may be occluded between the layers and either bonded to the structure itself or to the cations as a hydration shell. Commercially available clays of this type include bentonite, montmorillonite, hectorite, beidellite, nontronite, and a host of other smectite materials, from hundreds of localities, often having local names and specific compositions.

Normally, the clay structure yields repeating plates every 9 Å or thereabouts. Much work has been done to demonstrate that these platelets may be separated further, i.e., interlayered, by insertion of various polar molecules such as water, ethylene glycol, various amines, etc,. and that the platelets can be separated by as much as 30 to 40 Å.

The catalyst of the present invention may be obtained by reacting smectite type clays with polymeric cationic multimetal complexes. Such compositions are extensively discussed in U.S. Pat. No. 4,666,877 which is incorporated herein by reference.

The pillared interlayered clays of the present invention possess an internal microstructure which may be established by introducing discrete and non-continuous inorganic oxide particles or pillars having a length between about 5 and 20 Å, between the clay layers. These pillars serve to hold the space between the clay layers open after removal of included water and serve to form an internal interconnected micropore structure throughout the inner layer in which the majority of the pores are less than about 30 Å in diameter. The product interlayered clay may be produced by reacting a naturally occurring or synthetic smectite type clay with a polymeric cationic hydroxy multimetal complex, the complex being produced by reacting certain metal-containing compounds with materials such as aluminum chlorohydroxide complexes ("chlorhydrol", Reheis Chemical Co.), and heating to convert the hydrolyzed polymer complex into an inorganic multimetal oxide. The polymeric cationic hydroxy multimetal complex may be, of course, produced in a variety of other ways, including introducing additional metals into the initial aluminum solutions used in the polymer synthesis.

One method of obtaining the novel pillared interlayered clay catalysts of the present invention is to use the following general procedure:

(1) a cationic polymer of the type believed to be $(Al_{13}O_4(OH)_{24})^{7+}$, having a globular structure as first described by Johansen, *Acta. Chem. Scand.*, v. 14 (1960), p. 771, is reacted in aqueous solution with a 4th, 5th or 6th period transition metal salt. These will primarily be from Groups 5B, 6B, 7B and 8 of the Periodic Table. The base multiatomic complex is thought to be of the type:

In one form of the present invention, one or more of the noted elements may be substituted into either or both of the iv or vi coordinate Al sites in this molecular cluster. The general formula for the substituted molecule may be represented as:

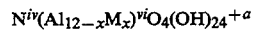

where N is selected from $Al^{3+}$, $Si^{4+}$, $Ga^{3+}$, $Ge^{4+}$, $As^{5+}$, $P^{5+}$, $Cr^{3+}$, $Fe^{3+}$, $V^{5+}$, $Ru^{4+}$, $Ni^{3+}$; and M is selected from one or more of the elements of Groups 5B, 6B 7B, and 8 of the 4th, 5th, or 6th Periods of the Periodic Table (see Kirk-Othmer *Encyclopedia of Chemical Technology*, 2nd Ed., vol. 8, (1965) for complete definition). The value for "x" may be from about 1 to about 6. The value for "a" depends upon the nature of the metal substitutions. Representative multimetal cationic polymer complexes include:

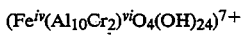

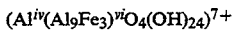

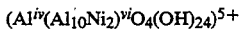

Obviously, such substitutions may change the charge on the polymer molecules. Depending upon the pH of the solution, such multimetallic molecules may be hydrolyzed to produce lower charged species as indicated by Vaughan et al; *Proc. 5th Intl. Zeolite Confi*, (1980), p. 94.

Another method for producing $(Al_{13})^{7+}$ substituted derivatives is discussed below and may be used as an alternative to beginning with a commercial solution of lower aluminum chlorhydrol.

(2) A smectite clay is mixed with the aqueous solution of polymeric cationic hydroxy multiatomic complex formed in step (1), in amounts so that the weight ratio of clay to metal complex solution is from about 1:2 to 1000. The metal complex solution will preferably contain from about 1 to about 40%, by weight, of solids in a suitable liquid medium such as water.

(3) The mixture of clay and metal complex is maintained at a temperature of about 5° C. to about 200° C. for a period of 0.1 to 4.0 hours.

(4) The reacted clay solids are recovered and heated at a temperature of from about 200° to about 700° C. to decompose the hydrolyzed metal complex to a pillar believed to be of multiple metallic oxides or hydroxides.

Depending on the nature of the reactant metal salts, the reactant concentrations and aging temperatures and pressures, alternative complexes may be formed in this reaction system to yield either larger or smaller metallic or multimetallic clusters.

After "setting" the pillar by calcination, it is possible to further increase the metal concentration between the layers of the pillared clay by exchanging said pillared clay with a solution containing cations of the metal to be exchanged. For example, by exchanging said pillared clay with a one tenth molar solution of $CrCl_3$, the chromium content of said pillared clay could be increased. Such post-exchange is also a way to control the residual acidity of the catalyst, as the metal cation will be titrating residual acidic protons in the pillared clay catalyst interlayer.

The pillared clay catalysts of the present invention may also be treated with a solution of $BF_3 \cdot xH_2O$, where x is 1 or 2. The pillared clay is treated with an aqueous solution of the above boron trifluoride hydrate by any suitable impregnation technique at an effective temperature and time which results in the desired degree of impregnation. Typical temperatures will range from about 0° C. to about 70° C., preferably from about 20° C. to about 35° C. Typical times will range from about 5 minutes to about 300 minutes, preferably from about 10 minutes to about 30 minutes.

The ethers of the present invention can be produced by first preparing a mixture of the tertiary alcohol and aliphatic alcohol. The alcohol mixture is then introduced into a suitable reaction vessel containing the catalyst wherein the reaction is conducted at a temperature from about ambient temperature (about 22° C.) to about 200° C., preferably from about 80° to 140° C., and a pressure from about 0 psig to about 1000 psig, preferably from about 150 psig to about 350 psig. A preferred type of reaction vessel is a tubular reactor. The reaction is conducted at an effective liquid hourly space velocity (LHSV). Such space velocities will normally range from about 0.5 to 10 LHSV, preferably from about 1 to 4 LHSV.

The following examples are presented for illustrative examples and are not to be considered as limiting the scope of the present invention in any way.

EXAMPLE 1

A chromium aluminum pillared clay was prepared from a commercial smectite clay (Bentolite L, Georgia Kaolin Co.). After first dissolving 53.2 gm (0.2 mole) $CrCl_3 \cdot 6H_2O$ in 42 gm $H_2O$ then adding 42 gm of a commercial 50 wt. % solution of the $[Al_{13}]^{7+}$ polymer ("chlorhydrol" Reheis Chemical Co.), followed by aging at room temperature for three days, 125 gm of the resulting blue solution was reacted with 5 gm Bentolite L at room temperature for 18 hours, at which time the product was vacuum filtered, and the filter coke washed with deionized water until the filtrate was colorless. This product was then freeze dried, then calcined at 450° C. X-ray diffraction analysis showed that the larger spacing (001) was 14.8 Å. To a 100 ml stirred batch reactor was added 200 mg of the Cr—Al pillared clay together with 5.51 gm (0.063 mole) tert-amyl alcohol and 3.96 gm (0.124 mole) methanol. After reacting the contents at 140° C. for 1 hour with stirring, the products were removed and analyzed by gas chromatography. The results are given in Table I below, showing moderate selectivity for TAME production and high selectivity for 2-methyl butenes at very high conversions for tert-amyl alcohol.

EXAMPLE 2

A cobalt-alumina pillared clay catalyst was made using the general method of Example 1 above, but using 46 gm $CoCl_2 \cdot 6H_2O$ dissolved in 46 gm $H_2O$ in place of the $CrCl_3$ solution. X-ray diffraction analysis showed the main basal reflection (001) to be a strong broad peak with a position at half maximum at 18.8 Å. Chemical analysis gave a composition of 72.2 wt. % $SiO_2$; 25.21 wt. % $Al_2O_3$ and 0.31 wt. % CoO compared to a base Bentolite L composition of 76.66 wt. % $SiO_2$ and 16.77 wt. % $Al_2O_3$ (all dry basis values). This represents an Al/Co ratio of about 35 in the pillar. Reacting 200 mg of this catalyst as described in Example 1 yielded the products shown in Table I, indicating high conversions and good selectivity for TAME.

EXAMPLE 3

A nickel-aluminum pillared clay catalyst was made using the general method of Example 1, but using 47.4 gm $NiCl_2 \cdot 6H_2O$ dissolved in 42 gm $H_2O$ in place of the $CrCl_3$ solution. X-ray diffraction analysis of the product showed a very broad strong peak between 20 Å and 14.8 Å, with the position at half maximum at 16.4 Å. Chemical analysis gave 72.97 wt. % $SiO_2$, 23.39 wt. % $Al_2O_3$ and 1.29 wt. % NiO, representing an Al/Ni ratio of 8.4 in the pillar. Reacting this catalyst in the identical manner to those in Examples 1 and 2 above yielded the results shown in Table I below, showing very high conversion and good TAME selectivity.

EXAMPLE 4

54 gm. $FeCl_3 \cdot 6H_2O$ were dissolved in 42 gm $H_2O$; the solution was filtered then added to 42 gm 50 wt. %

Al₁₃ chlorhydrol solution (Reheis Chemical Co.) and aged for 90 minutes at room temperature. To the resultant soft gel were added 42 gm H₂O with vigorous homogenization, then 5 gm Bentolite L. This was then freeze dried, yielding a catalyst having no X-ray diffraction peaks. Such a material comprises a highly delaminated clay admixed with an iron-aluminum oxide colloid. Such materials are said to have a "house-of-cards" structure, with little microporosity characteristic of pillared clays, and appreciable mesoporosity. Reacting this catalyst (Fe-clay) in the reaction described in Example 1 showed it to have low activity and poor selectivity (Table I below), confirming that the microporous properties of the metal pillared clay is important for improved catalytic performance.

TABLE I

Products Produced from the Reaction of Tert-Amyl Alcohol and Methanol

| Example | Catalyst | TAME (Mol %) | 2-Me-Butenes (Mol %) | Tert-amyl Alcohol Conversion |
|---|---|---|---|---|
| 1 | Cr-PILC* | 18.9 | 77.0 | 95.9 |
| 2 | Co-PILC | 28.2 | 40.0 | 68.2 |
| 3 | Ni-PILC | 30.1 | 46.6 | 76.7 |
| 4 | Fe-Clay | 18.1 | 22.4 | 40.5 |

*PILC = pillared clay

EXAMPLE 5

To a 100 mL stirred batch reactor is added either the Ni-PILC, made as described in Example 3, or a post-exchanged Ni-pillared clay [Ni(PILC)] made by exchanging 5 gm Al-PILC (typical of U.S. Pat. No. 4,271,043) with a solution of 2 gm NiO₂•6H₂O dissolved in 40 gm H₂O for 10 minutes at room temperature, followed by calcination for 1 hour at 400° C. X-ray diffraction analysis showed this to have a larger spacing (001) of 18.5 Å. (0.200 g), tert-amyl alcohol (5.51 g, 0.063 mol) and methanol (3.96 g, 0.124 mol). The contents are then sealed and heated to 140° C. with stirring for 1 hr. The exchanged Ni-PILC of Example 3 enhances tert-amyl alcohol conversion and TAME production (see Table II below). This implies that the pre-exchanged transition-metal pillared clays are more acidic than their post-exchanged counterparts, indicating that the Ni²⁺ post exchange titrates residual proton sites with Ni²⁺.

TABLE II

Effect of Transition-Metal Pillaring Preparation

| Catalyst | Preparation | TAME (Mol %) | 2-Me-Butenes (Mol %) | Tert-amyl Alcohol Conversion |
|---|---|---|---|---|
| Ni-PILC | Pre-exchanged | 30.1 | 46.6 | 76.7 |
| Ni(PILC) | Post-exchanged | 11.6 | 22.4 | 34.0 |

EXAMPLE 6

In a 100 mL stirred batch reactor the Cr-PILC, made as described in Example 1 (0.200 g), was reacted with various ratios of methanol/tert-amyl alcohol. The C₅ carbocation is more likely to undergo attack by MeOH compound. Thus TAME yields increase (nucleophilic pathway) while the formation of 2-Me-butenes decrease (elimination pathway) without loss in overall conversion (see Table III below).

TABLE III

Increased MeOH/Tert-Amyl Alcohol Ratio Increases TAME Selectivity with the CR-PILC

| MeOH/Tert-amyl Alcohol (eq) | TAME (Mol %) | 2-Me-Butenes (Mol %) | Tert-amyl Alcohol Conversion |
|---|---|---|---|
| 2 | 18.9 | 77.0 | 95.9 |
| 5 | 40.0 | 53.2 | 93.2 |
| 10 | 47.4 | 43.9 | 91.3 |

EXAMPLE 7

To a 100 mL stirred batch reactor is added the Cr-PILC, made as described in Example 1 (0.200 g), tert-amyl alcohol (5.51 g, 0.063 mol) and methanol (3.96 g, 0.124 mol). The contents are then sealed and heated at various temperatures with stirring for 1 hr (see Table IV below). As the temperature increases, the C₅ carbocation is less stable and more prone to elimination pathways producing more 2-Me-butenes. Although lower reaction temperatures favors TAME selectivity, tert-amyl alcohol conversion decreases. Longer reaction times at lower temperatures should show greater conversion and increased TAME selectivities.

TABLE IV

TAME Selectivity Increases as Temperatures Decreases with the Cr-PILC

| Temperature | TAME (Mol %) | 2-Me-Butenes (Mol %) | Tert-amyl Alcohol Conversion | Selectivity |
|---|---|---|---|---|
| 90 | 10.1 | 6.1 | 16.1 | 62.7% |
| 120 | 40.1 | 36.4 | 76.5 | 52.4% |
| 140 | 18.9 | 77.0 | 95.9 | 19.7% |

What is claimed is:

1. A process for preparing unsymmetrical dialkyl ethers, wherein one of the alkyl groups is a tertiary group, which process comprises reacting a C₁ to C₃ aliphatic alcohol with a tertiary alkyl alcohol, in the presence of a catalyst comprised of a transition metal pillared interlayered clay having generally separated layers wherein the interlayer distances are substantially greater than a precursor of the same but non-separated clay and wherein the product includes multimetallic pillars, comprised of a cationic polymeric complex, or derivative structure thereof, of the formula:

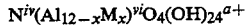

$$N^{iv}(Al_{12-x}M_x)^{vi}O_4(OH)_{24}{}^{a+}$$

where x is a number from 1 to 6; a depends on the selection of M and N; N is selected from Al³⁺, Si⁴⁺, Ga³⁺, Ge⁴⁺, As⁵⁺, P⁵⁺, Cr³⁺, Fe³⁺, V⁵⁺, Ru³⁺, Ru⁴⁺, Ni²⁺, and Co²⁺; and M is one or more of the elements of Groups 5B, 6B, 7B and 8 of the 4th, 5th and 6th Periods of the Periodic Table of the Elements.

2. The process of claim 1 wherein the tertiary alcohol is one in which two of the alkyl groups are methyl and the third is selected from the group consisting of methyl, ethyl, propyl, and butyl.

3. The process of claim 2 wherein the third alkyl group is selected from the group consisting of methyl and ethyl.

4. The process of claim 3 wherein the third alkyl group is an ethyl group.

5. The process of claim 2 wherein the aliphatic alcohol is methanol.

6. The process of claim 1 wherein H is Al.

7. A process for preparing unsymmetrical dialkyl ethers, wherein one of the alkyl groups is a tertiary group, which process comprises reacting a $C_1$ to $C_3$ aliphatic alcohol with a tertiary alcohol, in the presence of a catalyst comprised of a transition metal pillared interlayered clay having generally separated layers wherein the interlayer distances are substantially greater than a precursor of the same but non-separated clay and wherein the product includes multimetallic pillars comprised of a cationic polymeric complex, or derivative structure thereof, of the formula:

$$Al^{iv}(Al_{12-x}M_x)^{vi}O_4(OH)_{24}{}^{a+}$$

where x is a number from 1 to 6; a depends on the selection of M; and M is selected from the group consisting of Cr, Co and Ni.

8. The process of claim 7 wherein the tertiary alcohol is one in which two of the alkyl groups are methyl and the third is selected from methyl, ethyl, propyl, and butyl.

9. The process of claim 8 wherein the third alkyl group is selected from methyl and ethyl.

10. The process of claim 9 wherein the third alkyl group is an ethyl group.

11. The process of claim 7 wherein the aliphatic alcohol is methanol.

* * * * *